US011800986B2

United States Patent
Lin et al.

(10) Patent No.: US 11,800,986 B2
(45) Date of Patent: Oct. 31, 2023

(54) NON-PRESSURE CONTINUOUS BLOOD PRESSURE MEASURING DEVICE AND METHOD

(71) Applicant: INDUSTRIAL TECHNOLOGY RESEARCH INSTITUTE, Hsinchu (TW)

(72) Inventors: Hong-Dun Lin, Hsinchu (TW); Tai-Wei Su, Taoyuan (TW); Chun-Kai Chang, New Taipei (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 244 days.

(21) Appl. No.: 17/134,812

(22) Filed: Dec. 28, 2020

(65) Prior Publication Data
US 2022/0202299 A1   Jun. 30, 2022

(51) Int. Cl.
*A61B 5/021* (2006.01)
*A61B 5/05* (2021.01)
(Continued)

(52) U.S. Cl.
CPC ........ *A61B 5/02125* (2013.01); *A61B 5/0006* (2013.01); *A61B 5/02444* (2013.01);
(Continued)

(58) Field of Classification Search
CPC .............. A61B 5/02125; A61B 5/0006; A61B 5/02444; A61B 5/05; A61B 5/28;
(Continued)

(56) References Cited

U.S. PATENT DOCUMENTS

| 4,846,189 A | 7/1989 | Sun |
| 5,309,916 A | 5/1994 | Hatschek |

(Continued)

FOREIGN PATENT DOCUMENTS

| CN | 107257249 A | 10/2017 |
| CN | 108498081 A | 9/2018 |

(Continued)

OTHER PUBLICATIONS

Non-Contact Blood Pressure Measurement Scheme Using Doppler Radar Tomoyuki Ohata, Annu Int Conf IEEE Eng Med Biol Soc. Jul. 2019:778-781 (Year: 2019).*

(Continued)

*Primary Examiner* — Shahdeep Mohammed
*Assistant Examiner* — Fikirte (Fiki) T Ashine
(74) *Attorney, Agent, or Firm* — Maschoff Brennan

(57) ABSTRACT

A non-pressure continuous blood pressure measuring device, comprises: a radar sensing module, an electro-cardiac sensing module and a microprocessor. The radar sensing module includes at least a transmitter and a receiver, the transmitter continuously provides a pulse wave signal to an artery, the receiver receives a reflected pulse wave signal. The electro-cardiac sensing module includes at least an electrode; the electro-cardiac sensing module receives an electro-cardiac signal through the electrode. The microprocessor is in signal transmittable connection with the radar sensing module and the electro-cardiac sensing module. The microprocessor controls the radar sensing module and the electro-cardiac sensing module, and simultaneously receives the reflected pulse wave signal and the electro-cardiac signal. The microprocessor determines a blood pressure parameter of the artery according to the reflected pulse wave signal and the electrocardiography signal.

16 Claims, 5 Drawing Sheets

(51) Int. Cl.
*A61B 5/024* (2006.01)
*A61B 5/318* (2021.01)
*A61B 5/00* (2006.01)
*G16H 40/63* (2018.01)
*A61B 5/28* (2021.01)

(52) U.S. Cl.
CPC .................. *A61B 5/05* (2013.01); *A61B 5/28* (2021.01); *A61B 5/318* (2021.01); *A61B 5/7203* (2013.01); *A61B 5/7225* (2013.01); *A61B 5/7278* (2013.01); *A61B 5/7425* (2013.01); *G16H 40/63* (2018.01)

(58) Field of Classification Search
CPC ..... A61B 5/318; A61B 5/7203; A61B 5/7225; A61B 5/7278; A61B 5/7425; A61B 2505/07; A61B 2562/0228; A61B 5/002; A61B 5/0507; A61B 5/332; A61B 5/349; A61B 5/6823; G16H 40/63
See application file for complete search history.

(56) References Cited

U.S. PATENT DOCUMENTS

| | | |
|---|---|---|
| 6,852,083 B2 | 2/2005 | Caro et al. |
| 6,932,772 B2 | 8/2005 | Kan |
| 6,939,299 B1 | 9/2005 | Petersen et al. |
| 7,427,268 B2 | 9/2008 | Millay et al. |
| 7,674,231 B2 | 3/2010 | McCombie et al. |
| 8,162,841 B2 | 4/2012 | Keel et al. |
| 9,113,797 B2 | 8/2015 | Sankai |
| 10,542,894 B2 | 1/2020 | Zhao et al. |
| 2008/0045847 A1 | 2/2008 | Farag et al. |
| 2011/0208060 A1 | 8/2011 | Haase et al. |
| 2011/0307034 A1* | 12/2011 | Hastings ............ A61B 18/1492 607/61 |
| 2014/0343393 A1* | 11/2014 | Lee ...................... A61B 5/0082 600/407 |
| 2015/0157239 A1 | 6/2015 | Rissacher et al. |
| 2020/0000349 A1 | 1/2020 | Lin et al. |
| 2020/0029838 A1 | 1/2020 | Tang et al. |

FOREIGN PATENT DOCUMENTS

| | | |
|---|---|---|
| CN | 111856455 A | 10/2020 |
| TW | 201821023 A | 6/2018 |
| TW | 201907865 A | 3/2019 |
| TW | I653032 B | 3/2019 |
| WO | 2010/038120 A1 | 4/2010 |

OTHER PUBLICATIONS

Non-contact Acquisition of Respiration and Heart Rates Using Doppler Radar with Time Domain Peak-detection Algorithm Xiaofeng Yang, Guanghao Sun, Member, IEEE, Koichiro Ishibashi, Fellow, IEEE 2017 IEEE 2017 IEEE (Jul. 2017;2017:2847-2850) (Year: 2017).*
"Non-Contact Blood Pressure Measurement Scheme Using Doppler Radar" Tomoyuki Ohata, Annu Int Conf IEEE Eng Med Biol Soc. Jul. 2019:778-781 (Year: 2019) (Year: 2019).*
TW Office Action in Application No. 110100470 dated Nov. 16, 2021.
Avolio et al., 'Arterial Blood Pressure Measurement and Pulse Wave Analysis—Their Role in Enhancing Cardiovascular Assessment', Physiological Measurement, 31, R1-R47, 2010.
Gladdish et al., 'Repeatability of Non-Invasive Measurement of Intracerebral Pulse Wave Velocity Using Transcranial Doppler', Clinical Science, 433-439, Jun. 2005.
Kachuee et al., 'Cuff-Less Blood Pressure Estimation Algorithms for Continuous Health-Care Monitoring', IEEE Transactions on Biomedical Engineering, Jun. 2016.
Lopez et al., 'Continuous Blood Pressure Monitoring in Daily Life', Joint Conference on Micromechatronics for Information and Precision Equipment, Jun. 17-20, 2009.
McCombie et al., 'Adaptive Blood Pressure Estimation from Wearable PPG Sensors Using Peripheral Artery Pulse Wave Velocity Measurements and Multi-Channel Blind Identification of Local Arterial Dynamics', Proceedings of the 28th IEEE EMBS Annual International Conference, New York City, USA Aug. 30-Sep. 3, 2006.
Mohebbian et al., 'Blind, Cuff-less, Calibration-Free and Continuous Blood Pressure Estimation Using Optimized Inductive Group Method of Data Handling', Biomedical Signal Processing and Control, 57, 2020.
Padilla et al., Assessment of Relationships Between Blood Pressure, Pulse Wave Velocity and Digital Volume Pulse, Center for Research and Innovation on Bioengineering, Computers in Cardiology, 893-896, 2006.
Woodman et al., Interpretation of the Digital Volume Pulse: Its Relationship with Large and Small Artery Compliance, Clinical Science, Apr. 2003.
TW Office Action in Application No. 110100470 dated Jun. 20, 2022.
TW Office Action in Application No. 110100470 dated Feb. 17, 2022.
TW Office Action in Application No. 110100470 dated Jul. 2, 2021.
Lauteslager et al., "Cross-Body UWB Radar Sensing of Arterial Pulse Propagation and Ventricular Dynamics" Dec. 24, 2018, 2018 IEEE Biomedical Circuits and Systems.
TW Office Action in Application No. 110100470 dated Jan. 6, 2023.

* cited by examiner

NON-PRESSURE CONTINUOUS BLOOD PRESSURE MEASURING DEVICE AND METHOD

BACKGROUND

1. Technical Field

This disclosure relates to a non-pressure continuous blood pressure measuring device and method.

2. Related Art

Nowadays, cardiovascular disease is one of the greatest risks to modern society. Therefore, not only clinically, people are also paying more attention to their cardiovascular condition in daily life, and blood pressure is one of the important indicators for observing cardiovascular disease. Existing medical equipment for measuring blood pressure mainly are stethoscope and blood pressure meter that uses a cuff to measure blood pressure using the resonance method. The blood pressure meter indirectly measures discontinuous blood pressure mainly through inflating and deflating a cuff. If continuous blood pressure measurement is needed, then blood pressure is measured by repeatedly applying pressure with a cuff.

However, the blood pressure meter equipped with cuff is larger in size, which means it is inconvenient for the user to carry it around. Therefore, some manufactures have developed wrist-type blood pressure measuring device that uses an optical sensor to measure the blood flow changes in the blood vessels by photoplethysmography (PPG). When measuring blood pressure with the optical sensor, since optical sensor is susceptible to interference from external light sources, the optical sensor has to be tightly attached to the subject's skin during measurement.

SUMMARY

Accordingly, this disclosure provides a non-pressure continuous blood pressure measuring device and method.

According to one or more embodiment of this disclosure, a non-pressure continuous blood pressure measuring device, comprising: a radar sensing module, at least including a transmitter and a receiver, with the transmitter continuously providing a pulse wave signal to an artery, and the receiver receiving a reflected pulse wave signal; an electro-cardiac sensing module, at least including an electrode, with the electro-cardiac sensing module receiving an electro-cardiac signal through the electrode; and a microprocessor, in signal transmittable connection with the radar sensing module and the electro-cardiac sensing module, with the microprocessor controlling the radar sensing module and the electro-cardiac sensing module while receiving the reflected pulse wave signal and the electro-cardiac signal, and determining a blood pressure parameter according to a specific frequency band of the reflected pulse wave signal and the electro-cardiac signal.

According to one or more embodiment of this disclosure, a non-pressure continuous blood pressure measuring method, comprising the following steps: providing continuously, by a transmitter of a radar sensing module, a pulse wave signal to a position of an artery; controlling, by a microprocessor, a receiver to receive a reflected pulse wave signal, while controlling an electro-cardiac sensing module to receive an electro-cardiac signal through an electrode, wherein the microprocessor is in signal transmittable connection with the radar sensing module and the electro-cardiac sensing module; and determining, by the microprocessor, a blood pressure parameter according to a specific frequency band of the reflected pulse wave signal and the electro-cardiac signal.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

Figure 1:
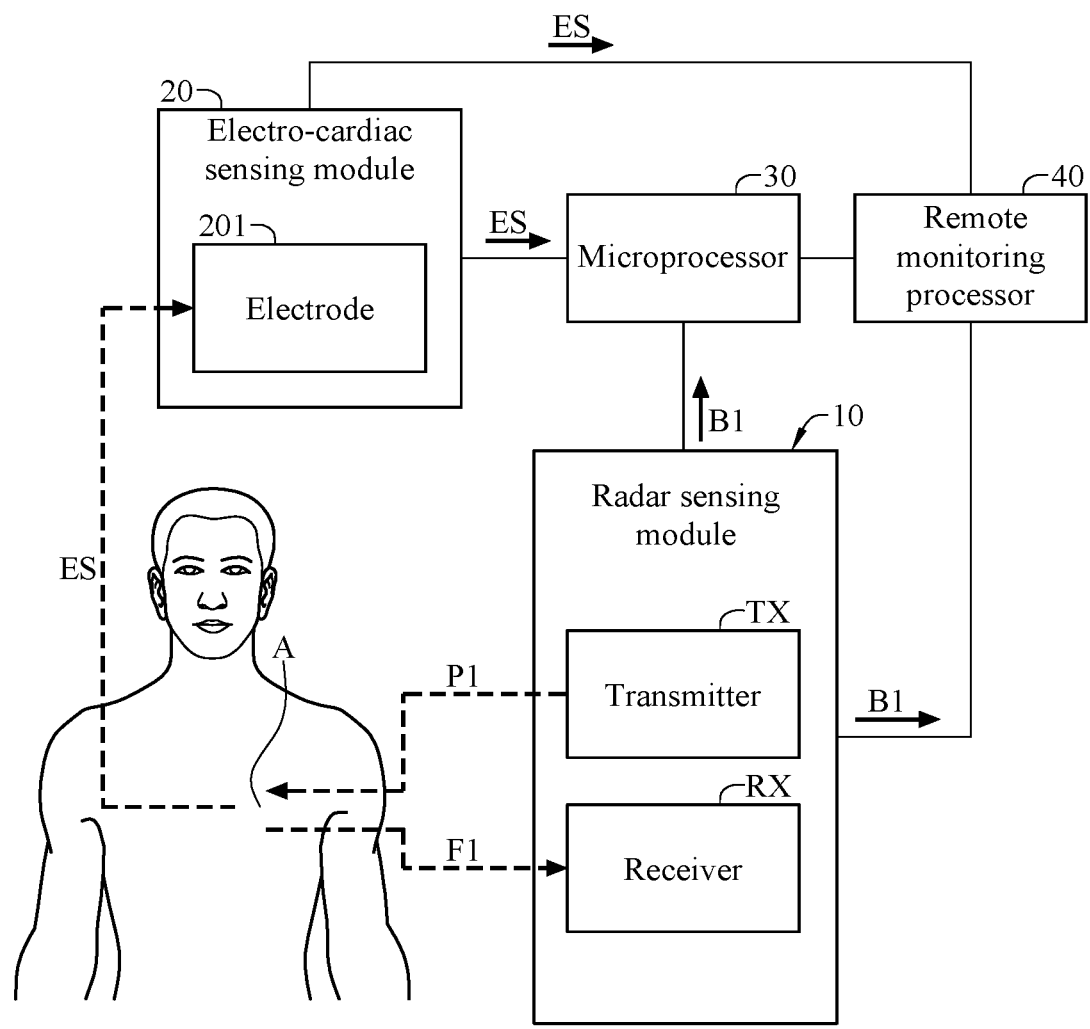
FIG. 1 is a block diagram of a non-pressure continuous blood pressure measuring device according to an embodiment of the present disclosure.

Please refer to FIG. 1, FIG. 1 is a block diagram of a non-pressure continuous blood pressure measuring device according to an embodiment of the present disclosure.

The non-pressure continuous blood pressure measuring device of the present disclosure comprises a radar sensing module 10, an electro-cardiac sensing module 20, and a microprocessor 30, wherein the radar sensing module 10 is, for example, a radar device that applies the principle of Doppler radar to transmit pulse wave signals and receive the reflected pulse wave signals; the electro-cardiac sensing module 20 is, for example, a sensor that can be configured to sense electro-cardiac signals; the microprocessor 30 is, for example, a processor or a controller that can process and analyze signals, and the microprocessor 30 is preferably disposed in a personal computer or a handheld device. The present disclosure does not limit the types of the radar sensing module 10, the electro-cardiac sensing module 20 and the microprocessor 30.

The radar sensing module 10 at least includes a transmitter TX and a receiver RX. The transmitter TX is configured to continuously transmit a pulse wave signal to the artery A. The receiver RX is configured to receive a reflected pulse wave signal that corresponds to the pulse wave signal, and the reflected pulse wave signal is preferably reflected from the artery A to the radar sensing module 10 for the receiver RX to receive. The artery A is, for example, one or more of aorta and non-aorta.

The electro-cardiac sensing module 20 comprises an electrode 201, and the electrode 210 is preferably dry electrode that is disposed in a dual-spot manner. The electrode 201 is configured to sense the electrical changes (such as voltage changes) on the skin surface caused by the depolarization of myocardial cells. The microprocessor 30 is in signal transmittable connection with the radar sensing module 10 and the electro-cardiac sensing module 20. That is, the microprocessor 30 can be in electrical connection with the radar sensing module 10 and the electro-cardiac sensing module 20, or the microprocessor 30 can be in connection with the radar sensing module 10 and the electro-cardiac sensing module 20 through internet, Bluetooth or other wireless manner, but the present disclosure is not limited thereto.

Figure 2:
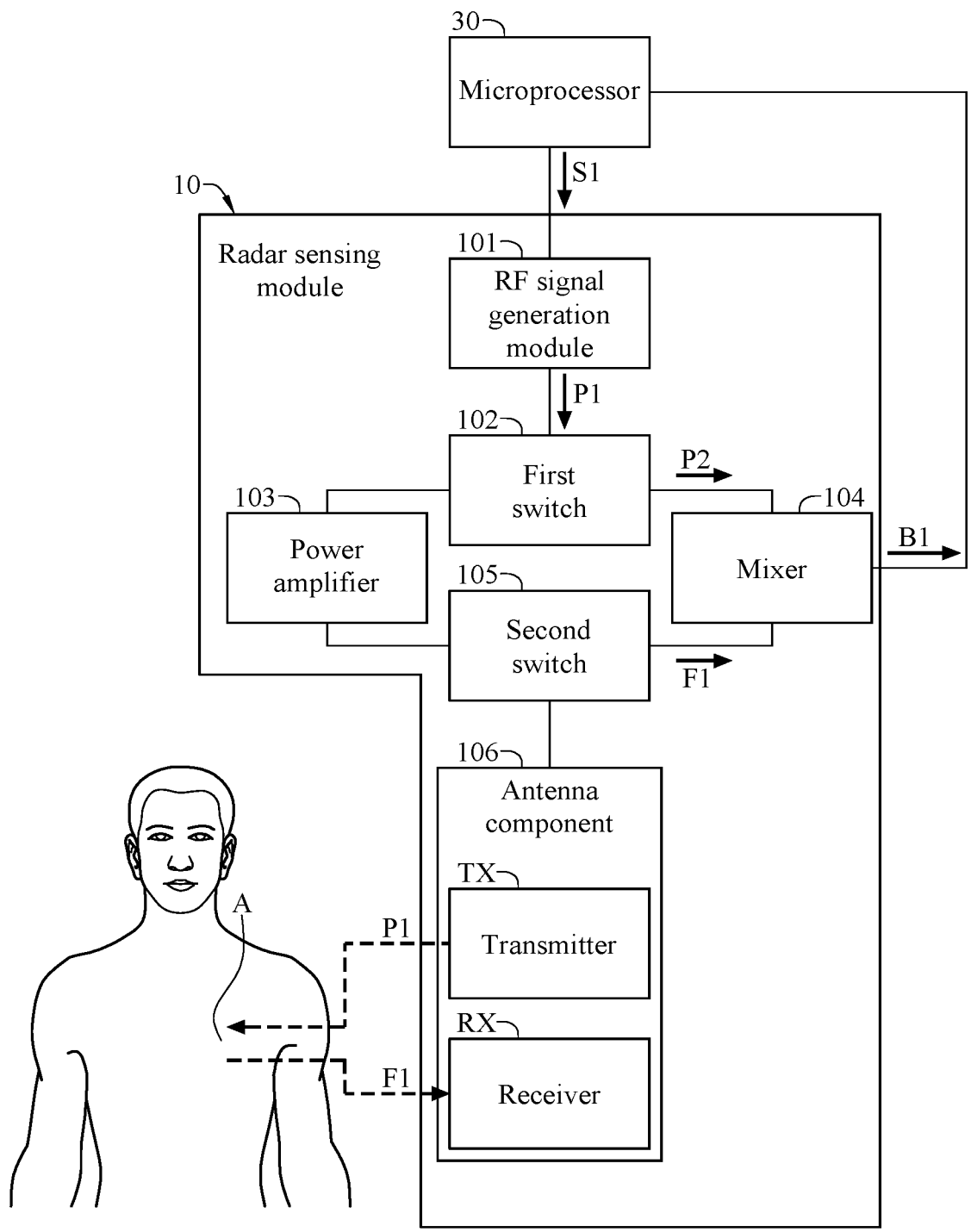
FIG. 2 is a block diagram of a radar sensing module according to an embodiment of the present disclosure.

Please refer to FIG. 2, wherein FIG. 2 is a block diagram of a radar sensing module according to an embodiment of the present disclosure. That is, FIG. 2 illustrates the block diagram of the radar sensing module 10 shown in FIG. 1. In detail, the radar sensing module 10 comprises a radio-frequency (RF) generation module 101, a first switch 102, a power amplifier 103, a mixer 104, a second switch 105 and an antenna component 106. The antenna component 106 comprises the transmitter TX and the receiver RX as shown in FIG. 1 as well as an antenna (now shown). The microprocessor 30 is in signal transmittable connection with the RF signal generation module 101 and the mixer 104, wherein the microprocessor 30 can output a pulse width modulation (PWM) signal.

The RF signal generation module 101 is connected to the first switch 102, and the first switch 102 is further connected to the power amplifier 103 and the mixer 104. The first switch 102 has a first state and a second state. When the first switch 102 is in the first state, the RF signal generation module 101 is electrically connected the power amplifier 103, and there is an open circuit between the RF signal generation module 101 and the mixer 104. When the first switch 102 is in the second state, the RF signal generation module 101 is electrically connected to the mixer 104, and there is an open circuit between the RF signal generation module 101 and the power amplifier 103.

The power amplifier 103 is connected to the second switch 105, and the second switch 105 is further connected to the mixer 104 and the antenna component 106. The second switch 105 has a third state and a fourth state. When the second switch 105 is in the third state, the power amplifier 103 is electrically connected to the antenna component 106, and there is an open circuit between the power amplifier 103 and the mixer 104. When the second switch 105 is in the fourth state, the antenna component 106 is electrically connected to the mixer 104, and there is an open circuit between the antenna component 106 and the power amplifier 103.

Further, the radar sensing module 10 can further comprise a first low noise amplifier (not shown) and a second low noise amplifier (not shown), wherein the first low noise amplifier is connected to both the first switch 102 and the mixer 104 with the first low noise amplifier locating between the first switch 102 and the mixer 104, and the second low noise amplifier is connected to both the second switch 105 and the mixer 104 with the second low noise amplifier locating between the second switch 105 and the mixer 104. Accordingly, a second pulse wave signal P2 and the reflected pulse wave signal F1 can be amplified, and the noise generated during the simultaneous amplification of the second pulse wave signal P2 and the reflected pulse wave signal F1 can be reduced.

In the embodiment shown in FIG. 1, the microprocessor 30 directly filters and amplifies the signal (the first blood vessel signal B1) outputted from the mixer 104. However, when the microprocessor 30 does not perform filtering and amplifying signal (for example, a low cost microprocessor that is unable to perform filtering and amplification signal is deployed as the microprocessor 30 in the non-pressure continuous blood pressure measuring device of the present disclosure), a filtering and amplifying module which includes a filter and an amplifier can be disposed to process the first blood vessel signal B1 to obtain a specific frequency band of the first blood vessel signal B1.

Further, the RF signal generation module 101, the first switch 102, the power amplifier 103, the mixer 104 and the second switch 105 can be integrated into an integrated circuit along with the microprocessor 30, thereby achieving a minimized non-pressure continuous blood pressure measuring device and its radar sensing module 10.

Please refer back to FIGS. 1 and 2, the microprocessor 30 can modulate the time interval of transmitting the pulse wave signals performed by the RF signal generation module 101, and modulate the time interval of sensing the electro-cardiac signal performed by the electrode 201, thereby continuously receiving the reflected pulse wave signal and the electro-cardiac signal.

The radar sensing module 10 and the electro-cardiac sensing module 20 can further be in signal transmittable connection with a remote monitoring processor 40, to transmit the reflected pulse wave signal F1 and the electro-cardiac signal ES to the remote monitoring processor 40 in a wireless manner. The display of the remote monitoring processor 40 can display the reflected pulse wave signal F1 and the electro-cardiac signal ES. The radar sensing module 10, the electro-cardiac sensing module 20 and the remote monitoring processor 40 each have an individual power supply. In addition, the remote monitoring processor 40 can also be in signal transmittable connection with the microprocessor 30, for the display of the remote monitoring processor 40 to display the part of the first blood vessel signal B1 in the specific frequency band received from the microprocessor 30.

Figure 3:
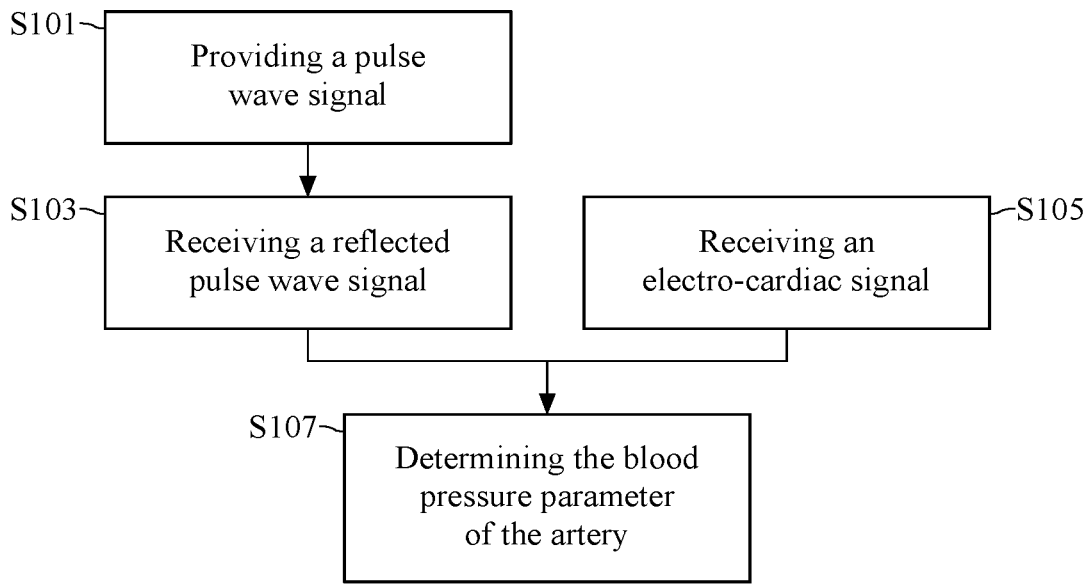
FIG. 3 is a flowchart of a non-pressure continuous blood pressure measuring method according to an embodiment of the present disclosure.

Please refer to FIGS. 1 to 3, wherein FIG. 3 is a flowchart of a non-pressure continuous blood pressure measuring method according to an embodiment of the present disclosure.

Step S101: Providing a pulse wave signal.

The microprocessor 30 controls the radar sensing module 10 continuously providing the pulse wave signal to the artery A. When the RF signal generation module 101 receives a first period signal 51 (for example, square wave) in the pulse width modulation (PWM) signal from the microprocessor 30, the RF signal generation module 101 transforms the first period signal 51 into a first pulse wave signal P1 with a surge. The frequency of the first pulse wave signal P1 is the same as that of the first period signal 51, and the waveform of the first pulse wave signal P1 is different from that of the first period signal 51.

When the first switch 102 receives the first pulse wave signal P1, the first switch 102 is in the first state, which allows the first pulse wave signal P1 to be transmitted to the power amplifier 103 through the first switch 102. That is, when the first pulse wave signal P1 is outputted from the first switch 102, the first switch 102 switches from the first state to the second state. When the power amplifier 103 receives the first pulse wave signal P1, the power amplifier 103 can amplify the first pulse wave signal P1. Then, the power amplifier 103 outputs the amplified first pulse wave signal P1 to the second switch 105. When the second switch 105 receives the amplified first pulse wave signal P1, the second switch 105 switches to the third state, thereby transmitting the first pulse wave signal P1 to the antenna component 106 through the second switch 105. When the antenna component 106 receives the first pulse wave signal P1, the transmitter TX of the antenna component 106 is configured to transmit the first pulse wave signal P1 to the artery A to measure the vibration frequency of the artery wall of the artery A. In the present embodiment, the frequency band of the first pulse wave signal P1 transmitted by the transmitter TX of the antenna component 106 can be 300 MHZ to 500 MHZ, but the present disclosure is not limited thereto. Since the outputted first pulse wave signal P1 is microwave with short pulse and low power, the pulse wave signal is unlikely to cause any harm to the subject.

Step S103: Receiving a reflected pulse wave signal.

The microprocessor 30 controls the receiver RX of the antenna component 106 to receive the reflected pulse wave signal F1 reflected from the artery A. In detail, after the first pulse wave signal P1 outputted by the antenna component 106 reaches the artery A, the reflected pulse wave signal F1 is reflected from the artery A. when the receiver RX of the antenna component 106 receives the reflected pulse wave signal F1 from the artery A, the antenna component 106 can transmit the reflected pulse wave signal F1 to the second switch 105, wherein the transmitter TX and the receiver RX have different angular position on the antenna component 106. When the second switch 105 receives the reflected pulse wave signal F1, the second switch 105 switches from the third state into the fourth state, while the first switch 102 in the second state receives a second pulse wave signal P2 from the RF signal generation module 101. The timing of the second pulse wave signal P2 is one period later than that of the first pulse wave signal P1 and has the same waveform as the first pulse wave signal P1. The RF signal generation module 101 generates the second pulse wave signal P2 according to the second period signal in the PWM signal coming from the microprocessor 30, wherein the timing of the second period signal is one period later than that of the first period signal 51 and has the same waveform as the first period signal 51.

At the meantime, the first switch 102 is in the second state and the second switch 105 is in the fourth state, and therefore, the mixer 104 receives the second pulse wave signal P2 and the reflected pulse wave signal F1 at the same time. Subsequently, the microprocessor 30 controls the mixer 104 to demodulate the second pulse wave signal P2 and the reflected pulse wave signal F1 to generate the first blood vessel signal B1 associated with the artery A.

Step S105: Receiving an electro-cardiac signal. The microprocessor 30 controls the electro-cardiac sensing module 20 to receive the electro-cardiac signal ES through the electrode 201. In addition, since the first pulse wave signal P1 provided by the radar sensing module 10 does not interfere with the electrode 201, the microprocessor 30 can control the receiver RX of the antenna component 106 and the electrode 201 of the electro-cardiac sensing module 20 to receive signals at the same time. That is, steps S103 and S105 can be performed simultaneously.

Step S107: Determining the blood pressure parameter of the artery.

As described above, since the first blood vessel signal B1 and the electro-cardiac signal ES each has a part corresponding to the specific frequency band, and the first blood vessel signal B1 further reflects the vibration frequency of the artery wall, the microprocessor 30 can determine the blood pressure parameter of the artery A based on the part of the first blood vessel signal B1 corresponding to the specific frequency band and the part of the electro-cardiac signal ES received from the electro-cardiac sensing module 20 as shown in FIG. 1.

Figure 4:
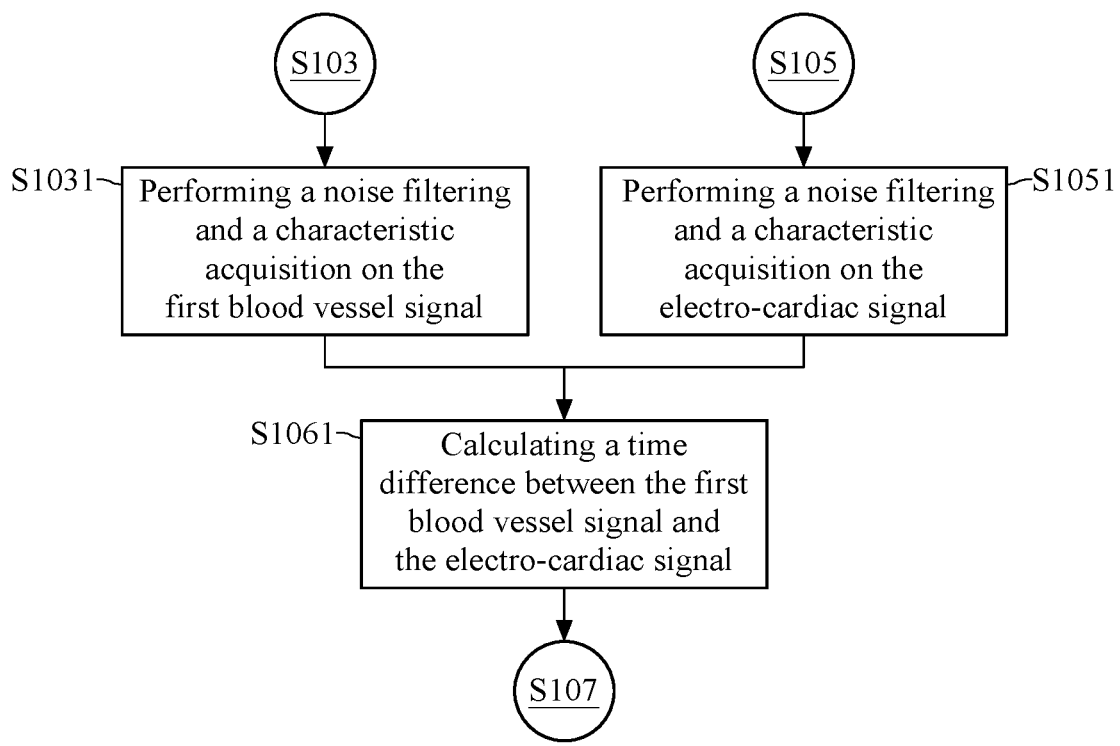
FIG. 4 is a flowchart of a non-pressure continuous blood pressure measuring method according to another embodiment of the present disclosure.
Figure 5:
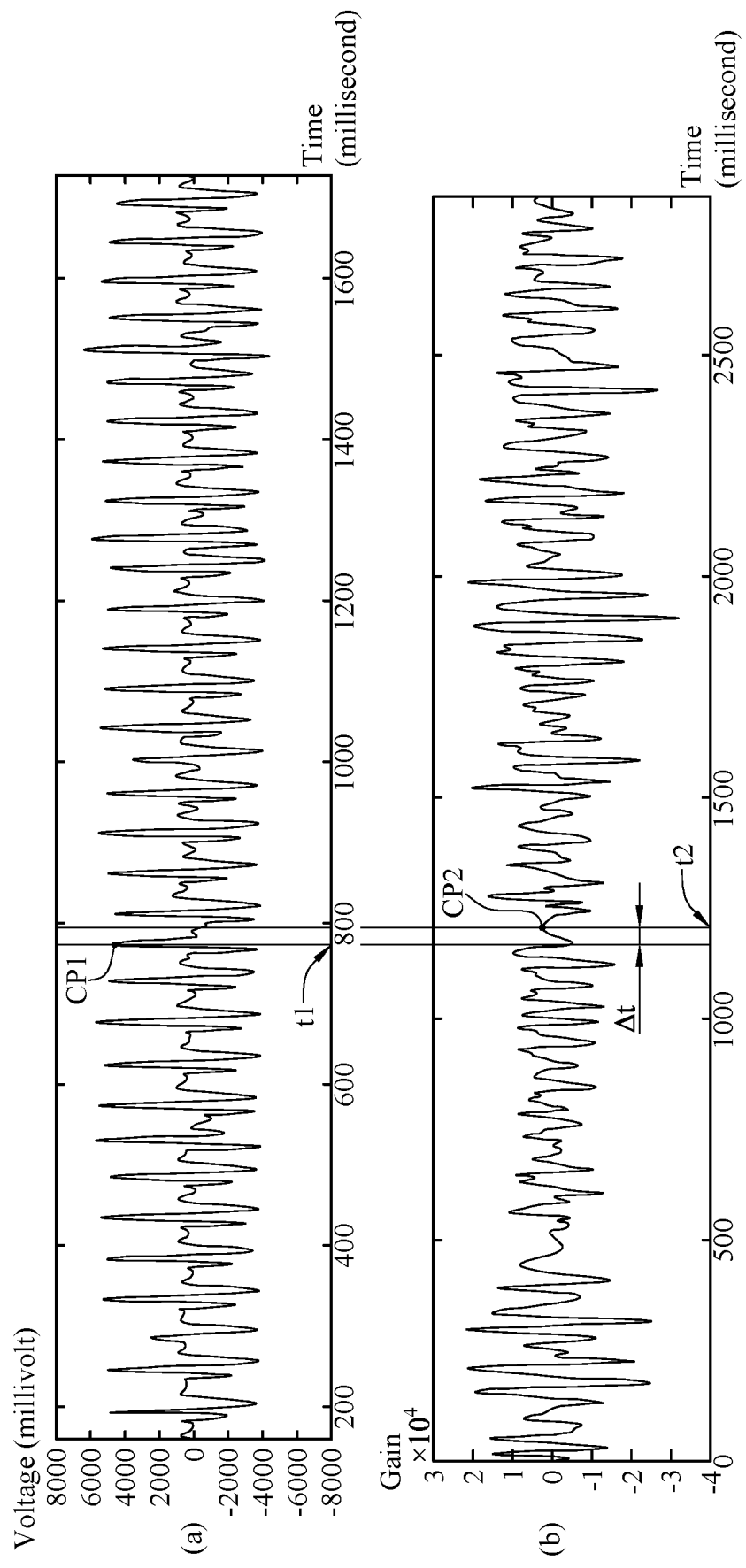
FIG. 5 illustrates diagrams showing waveforms of the blood vessel signal and electro-cardiac signal with a specific frequency band according to an embodiment of the present disclosure.

That is, please refer to FIGS. 4 and 5, FIG. 4 is a flowchart of a non-pressure continuous blood pressure measuring method according to another embodiment of the present disclosure; and FIG. 5 illustrates diagrams showing waveforms of the blood vessel signal and electro-cardiac signal with a specific frequency band according to an embodiment of the present disclosure.

Step S1031: Performing a noise filtering and a characteristic acquisition on the first blood vessel signal; step S1051: Performing a noise filtering and a characteristic acquisition on the electro-cardiac signal ES.

Please refer to both FIGS. 1 and 2, as described above, the microprocessor 30 can filter out the noise in the first blood vessel signal B1 and perform band pass filtering to extract the part of the first blood vessel signal B1 in the specific frequency band, as well as filter out the noise in the electro-cardiac signal ES and perform band pass filtering to extract the part of the electro-cardiac signal ES in the specific frequency band, wherein the specific frequency band extracted by performing band pass filtering is 0.8 Hz to 4 Hz. The microprocessor 30 acquire characteristic of the first blood vessel signal B1 and the electro-cardiac signal ES with the specific frequency band. As shown in FIG. 5, part (a) shows the electro-cardiac signal ES with the specific frequency band; part (b) shows the reflected pulse wave signal (the first blood vessel signal B1) with the specific frequency band, and both part (a) and part (b) are exemplary diagrams performed with characteristic acquisition.

Please first refer part (a) for an exemplary diagram of electrocardiography (ECG) composed of a plurality of consecutive electro-cardiac signal ES. The electro-cardiac signal ES is a continuous wave and has P, R, Q, S and T waves. The unit of the horizontal axis of the ECG shown is time (millisecond), and the unit of the vertical axis of the ECG is voltage (millivolt). The characteristic acquired by the microprocessor 30 can be one of the peaks of the continuous wave. In this example, the microprocessor 30 acquires the peak of the R wave in the ECG, and the horizontal axis that the peak of the acquired R wave corresponds to is a first time point t1, wherein the peak of the R wave acquired by the microprocessor 30 is represented as a first characteristic point CP1.

Please refer to the part of the reflected pulse wave signal (first blood vessel signal B1) in the specific frequency band as shown in part (b). The first blood vessel signal B1 is a continuous wave, the unit of the horizontal axis is time (millisecond), and the unit of the vertical axis is gain. The microprocessor 30 can acquire the characteristics of the first blood vessel signal B1 according to the first characteristic point CP1. That is, the microprocessor 30 can acquire the peak that is the closest to and later than the first time point t1, and use the peak as a second characteristic point CP2, wherein the horizontal axis that the second characteristic point CP2 corresponds to is a second time point t2. It should be noted that, the microprocessor 30 can also acquire the wave trough of R wave as the first characteristic point CP1, and acquire the wave trough that the first blood vessel signal B1 corresponds to as the second characteristic point CP2, the present disclosure is not limited thereto.

Step S1061: Calculating a time difference between the first blood vessel signal and the electro-cardiac signal.

The microprocessor 30 can calculate the time difference between the peak of the part of the first blood vessel signal B1 in the specific frequency band and the peak of the electro-cardiac signal ES. Take parts (a) and (b) of FIG. 5 for example, there is a time difference Δt between the first time point t1 of the first characteristic point CP1 of the electro-cardiac signal ES and the second time point t2 of the second characteristic point CP2 of the first blood vessel signal B1. The time difference $\Delta t$ is the time interval that the first blood vessel signal B1 arrives. The microprocessor 30 can calculate the blood pressure parameter of the artery Abased on the time difference $\Delta t$, wherein the blood pressure parameter includes a systolic blood pressure and/or a diastolic blood pressure.

First take systolic blood pressure as an example, the microprocessor 30 can calculate the systolic blood pressure using a systolic pressure equation, and the systolic pressure equation is:

$$BP_{sys}=a_1 \times PWV+b_1$$

wherein, $BP_{sys}$ is the systolic blood pressure; $a_1$ is a pulse wave velocity weighting factor; PWV is a pulse wave velocity; $b_1$ is a linear weighting factor.

That is, the electro-cardiac sensing module 20 is preferably in contact with the chest where the aorta is located; and the radar sensing module 10 is preferably near the chest where the aorta is located but not in direct contact with the chest. Further, the radar sensing module 10 and the electro-cardiac sensing module 20 are disposed with a distance therebetween. Therefore, the microprocessor 30 can divide the distance by the time difference $\Delta t$ to calculate pulse wave velocity PWV.

The pulse wave velocity weighting factor $a_1$ and the linear weighting factor $b_1$ are for reflecting the real blood flow condition and arterial condition. Specifically, even in a static state, the waveform of the electro-cardiac signal measured from each person is different, and the waveform of the measured reflected pulse wave signal is also different due to factors such as blood turbidity and vascular elasticity of each person.

Therefore, the microprocessor 30 can first obtain a plurality of electro-cardiac signals and a plurality of reflected pulse wave signals, and calculate the initial pulse wave velocity weighting factor and the initial linear weighting factor based on the electro-cardiac signals and the reflected pulse wave signals. The microprocessor 30 uses the initial linear weighting factor as the predetermined pulse wave velocity weighting factor $a_1$, and the initial linear weighting factor as the predetermined linear weighting factor $b_1$. After comparing the systolic blood pressure $BP_{sys}$ calculated from the systolic pressure equation and the systolic blood pressure measured from the blood pressure meter, the microprocessor 30 can adjust the pulse wave velocity weighting factor $a_1$ and the linear weighting factor $b_1$, so that the calculated systolic blood pressure $BP_{sys}$ using the pulse wave velocity weighting factor $a_1$ and the linear weighting factor $b_1$ can be more in line with the actual systolic blood pressure.

Similarly, the microprocessor 30 can calculate the diastolic blood pressure by using a diastolic pressure equation, and the diastolic pressure equation is:

$$BP_{Dia}=a_2 \times PWV+b_2$$

wherein, $BP_{Dia}$ is the diastolic blood pressure; $a_2$ is a pulse wave velocity weighting factor; PWV is a pulse wave velocity; $b_2$ is a linear weighting factor, wherein the pulse wave velocity PWV is calculated through dividing said distance by the time difference $\Delta t$ as described above. The microprocessor 30 can also use the initial linear weighting factor as the predetermined pulse wave velocity weighting factor $a_2$, and the initial linear weighting factor as the predetermined linear weighting factor $b_2$ in the same manner as described above. And similar to above, the microprocessor 30 can adjust the pulse wave velocity weighting factor $a_2$ and the linear weighting factor $b_2$ according to the comparison result of the diastolic blood pressure $BP_{Dia}$ calculated from the diastolic pressure equation and the diastolic blood pressure measured from the blood pressure meter. Therefore, the calculated diastolic blood pressure $BP_{Dia}$, using the pulse wave velocity weighting factor $a_2$ and the linear weighting factor $b_2$ can be more in line with the actual diastolic blood pressure.

In summary of calculating systolic blood pressure and the diastolic blood pressure according to the pulse wave velocity weighting factors $a_1$, $a_2$ and the linear weighting factors $b_1$, $b_2$, suitable pulse wave velocity weighting factors $a_1$, $a_2$ the linear weighting factors $b_1$, $b_2$ can be applied according to the subjects traits such as gender, age, etc., thereby the systolic blood pressure and the diastolic blood pressure close to the actual value can be calculated.

Figure 6:
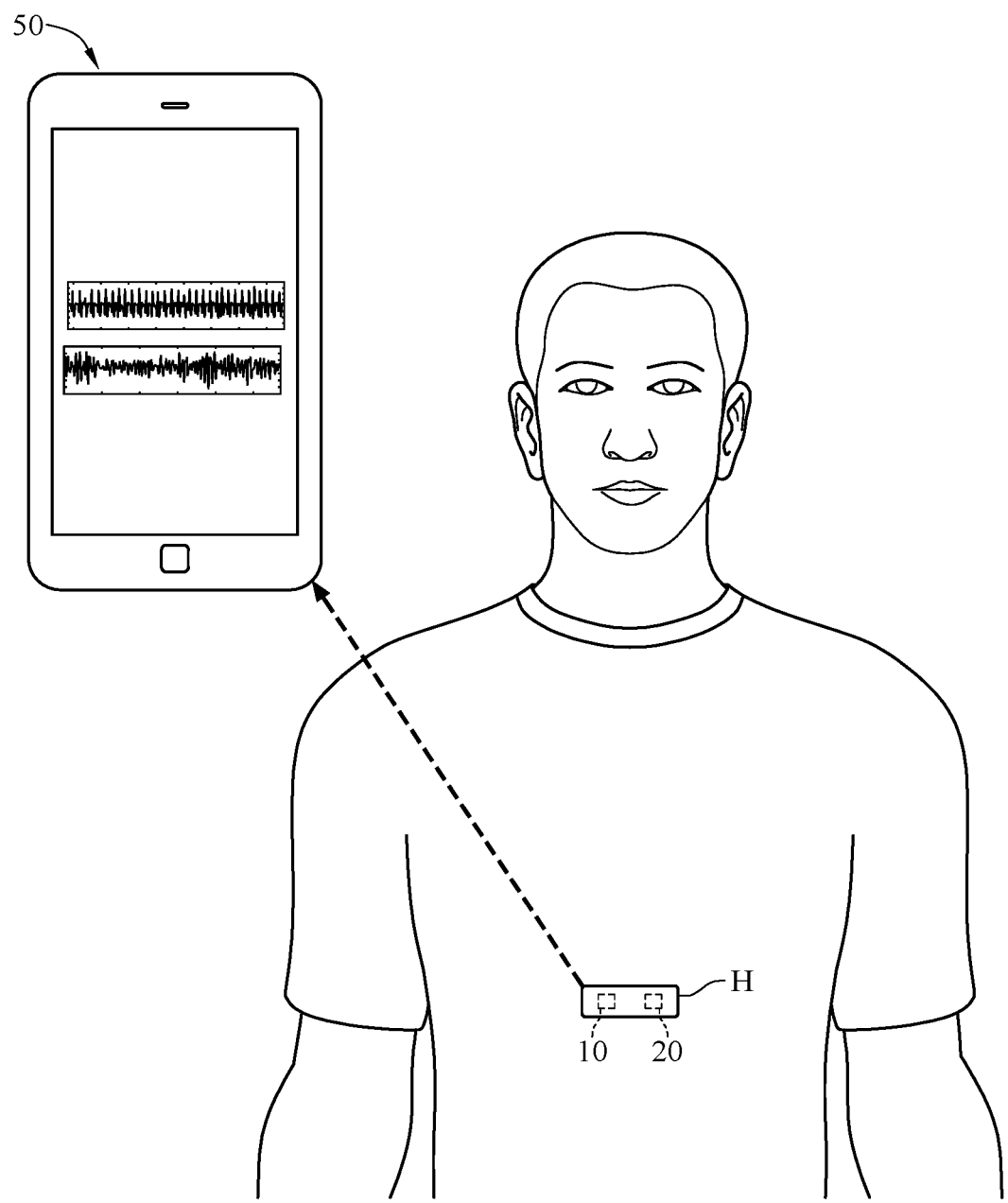
FIG. 6 is a diagram showing an actual application of non-pressure continuous blood pressure measuring device according to an embodiment of the present disclosure.

Further, please refer to FIG. 6, FIG. 6 is a diagram showing an actual application of non-pressure continuous blood pressure measuring device according to an embodiment of the present disclosure.

The radar sensing module 10 and the electro-cardiac sensing module 20 can be together disposed in a housing shell H. The housing shell H containing the radar sensing module 10 and the electro-cardiac sensing module 20 can be worn or attached to clothing. Therefore, the radar sensing module 10 and the electro-cardiac sensing module 20 can directly measure the reflected pulse wave signal F1 and the electro-cardiac signal ES from the subject. In addition, the microprocessor 30 (not illustrated in FIG. 6) of the mobile device 50 can control the radar sensing module 10 and the electro-cardiac sensing module 20 through wireless means, such as the Internet or Bluetooth. The sensed signals can also be transmitted to the microprocessor 30 of the mobile device 50 in the wireless way, so that the microprocessor 30 of the mobile device 50 can calculate the blood pressure parameter.

In view of the above description, according to one or more embodiments of the non-pressure continuous blood pressure measuring device and method of the present disclosure, blood pressure may be measured continuously while avoid the discomfort caused by traditional blood pressure meters that measure blood pressure by apply pressure to the subject, and even a person who's not a medical profession may also measure blood pressure easily. Further, users are allowed to measure blood pressure at any time, which increases the convenience of usage. In addition, according to one or more embodiments of the non-pressure continuous blood pressure measuring device and method of the present disclosure, since the blood vessel signal may be detected without direct contact with the subject's skin, the measurement is easier to carry out and the subject may feel more comfortable while his/hers blood pressure is being measured. Moreover, external signals may not cause interference during the measurement process. Therefore, through sensing the blood vessel signal and the electro-cardiac signal with the specific frequency band, the blood pressure subsequently calculated may be more accurate.

The present disclosure has been disclosed above in the embodiments described above, however it is not intended to limit the present disclosure. It is within the scope of the present disclosure to be modified without deviating from the essence and scope of it. It is intended that the scope of the present disclosure is defined by the following claims and their equivalents.

What is claimed is:

1. A non-pressure continuous blood pressure measuring device, comprising:
   radar sensing module, at least including a radio-frequency (RF) signal generation module, a first switch, a second switch a power amplifier, an antenna component and a mixer, wherein the antenna component comprises a transmitter and a receiver, the first switch is connected to the RF signal generation module, the power amplifier and the mixer, the second switch is connected to the power amplifier, the mixer and the antenna component, and wherein the first switch is in a first state after the RF signal generation module outputs a first pulse wave signal for the RF signal generation module to be electrically connected to the power amplifier, and for an open circuit to form between the RF signal generation module and the mixer, the RF signal generation module transmits the first pulse wave signal to the power amplifier through the first switch, the first switch is in a second state after the first switch outputting the first pulse wave signal for the RF signal generation module to be electrically connected to the mixer, and for an open circuit to form between the RF signal generation module and the power amplifier, the power amplifier amplifies the first pulse wave signal and outputs the first pulse wave signal that is amplified to the second switch, for the second switch to be in a third state which causes the power amplifier to be electrically connected to the antenna component and an open circuit is formed between the power amplifier and the mixer, the power amplifier outputs the first pulse wave signal that is amplified to the antenna component through the second switch, the transmitter transmits the first pulse wave signal that is amplified to an artery, and the receiver receives a reflected pulse wave signal corresponding to the first pulse wave signal that is amplified from the artery, and the antenna component transmits the reflected pulse wave signal to the second switch for the second switch to switch from the third state into a fourth state for the antenna component to be electrically connected to the mixer, and an open circuit is formed between the antenna component and the power amplifier, wherein the RF signal generation further generates a second pulse wave signal with a timing that is later than a timing of the first pulse wave signal;
   an electro-cardiac sensing module, at least including an electrode, with the electro-cardiac sensing module receiving an electro-cardiac signal through the electrode; and
   a microprocessor, in signal transmittable connection with the radar sensing module and the electro-cardiac sensing module, with the microprocessor controlling the radar sensing module and the electro-cardiac sensing module while receiving the electro-cardiac signal, wherein the microprocessor is configured to control the mixer to perform demodulation on the second pulse wave signal and the reflected pulse wave signal to generate a blood vessel signal associated with the artery, and
   determining a blood pressure parameter according to a specific frequency band of the blood vessel signal and the electro-cardiac signal.

2. The non-pressure continuous blood pressure measuring device according to claim 1, wherein the radar sensing module and the electro-cardiac sensing module respectively wirelessly transmit the reflected pulse wave signal and the electro-cardiac signal to a remote monitoring processor to display the signals; wherein, the radar sensing module, the electro-cardiac sensing module and the remote monitoring processor each has an individual power supply.

3. The non-pressure continuous blood pressure measuring device according to claim 1, wherein, the microprocessor modulates a time interval to receive the reflected pulse wave signal and the electro-cardiac signal, and performs a signal processing procedure on the reflected pulse wave signal and the electro-cardiac signal to obtain the specific frequency band.

4. The non-pressure continuous blood pressure measuring device according to claim 3, wherein, the signal processing procedure is a noise filtering, a characteristic acquisition and a time difference calculation; wherein, the time difference calculation is to calculate a time difference between the reflected pulse wave signal and the electro-cardiac signal corresponding to the specific frequency band.

5. The non-pressure continuous blood pressure measuring device according to claim 1, wherein, the microprocessor is disposed in a personal computer or a handheld device.

6. The non-pressure continuous blood pressure measuring device according to claim 1, wherein, the artery is one or more of aorta and non-aorta.

7. The non-pressure continuous blood pressure measuring device according to claim 1, wherein, the blood pressure parameter comprises a systolic blood pressure, the systolic blood pressure is calculated through a systolic pressure equation, and the systolic pressure equation is:

$$BP_{sys}=a_1 \times PWV + b_1$$

wherein, $BP_{sys}$ is the systolic blood pressure; $a_1$ is a pulse wave velocity weighting factor; PWV is a pulse wave velocity; $b_1$ is a linear weighting factor.

8. The non-pressure continuous blood pressure measuring device according to claim 1, wherein, the blood pressure parameter comprises a diastolic blood pressure, the diastolic blood pressure is calculated through a diastolic pressure equation, and the diastolic pressure equation is:

$$BP_{Dia}=a_2 \times PWV + b_2$$

wherein, $BP_{Dia}$ is the diastolic blood pressure; $a_2$ is a pulse wave velocity weighting factor; PWV is a pulse wave velocity; $b_2$ is a linear weighting factor.

9. A non-pressure continuous blood pressure measuring method, comprising the following steps:
   outputting, by a radio-frequency (RF) signal generation module of a radar sensing module, a first pulse wave signal to a first switch, wherein the first switch is connected to the RF signal generation module, a power amplifier and a mixer, and the first pulse wave signal causes the first switch to be in a first state for the RF signal generation module to be electrically connected to the power amplifier, and for an open circuit to form between the RF signal generation module and the mixer;
   transmitting, by the RF signal generation module, the first pulse wave signal to the power amplifier through the first switch, wherein the first switch is in a second state after the first switch outputting the first pulse wave signal for the RF signal generation module to be electrically connected to the mixer, and for an open circuit to form between the RF signal generation module and the power amplifier;
   amplifying, by the power amplifier, the first pulse wave signal and outputting, by the power amplifier, the first pulse wave signal that is amplified to a second switch to output the first pulse wave signal that is amplified to an antenna component, wherein the second switch is connected to the power amplifier, the mixer and the antenna component, the antenna component comprises a transmitter and a receiver, the first pulse wave signal that is amplified is outputted to the second switch for the second switch to be in a third state which causes the power amplifier to be electrically connected to the antenna component and an open circuit is formed between the power amplifier and the mixer;

transmitting, by the transmitter, the first pulse wave signal that is amplified to a position of an artery;

generating, by the RF signal generation module, a second pulse wave signal, wherein a timing of the second pulse wave signal is later than a timing of the first pulse wave signal;

controlling, by a microprocessor, the receiver to receive a reflected pulse wave signal corresponding to the first pulse wave signal that is amplified from the artery, while controlling an electro-cardiac sensing module to receive an electro-cardiac signal through an electrode, wherein the microprocessor is in signal transmittable connection with the radar sensing module and the electro-cardiac sensing module;

transmitting, by the antenna component, the reflected pulse wave signal to the second switch for the second switch to switch from the third state into a fourth state for the antenna component to be electrically connected to the mixer, and an open circuit is formed between the antenna component and the power amplifier; and controlling, by the microprocessor, the mixer to perform demodulation on the second pulse wave signal and the reflected pulse wave signal to generate a blood vessel signal associated with the artery, and determining, by the microprocessor, a blood pressure parameter according to a specific frequency band of the blood vessel signal and the electro-cardiac signal.

10. The non-pressure continuous blood pressure measuring method according to claim 9, wherein, the radar sensing module and the electro-cardiac sensing module respectively wirelessly transmit the reflected pulse wave signal and the electro-cardiac signal to a remote monitoring processor to display the signals.

11. The non-pressure continuous blood pressure measuring method according to claim 9, wherein, the microprocessor modulates a time interval to receive the reflected pulse wave signal and the electro-cardiac signal, and performs a signal processing procedure on the reflected pulse wave signal and the electro-cardiac signal to obtain the reflected pulse wave signal and the electro-cardiac signal corresponding to the specific frequency band.

12. The non-pressure continuous blood pressure measuring method according to claim 11, wherein, the signal processing procedure comprises:
performing a noise filtering and a characteristic acquisition respectively on the reflected pulse wave signal and the electro-cardiac signal;
calculating a time difference between the reflected pulse wave signal and the electro-cardiac signal that have been respectively performed with the noise filtering and the characteristic acquisition; and
calculating the blood pressure parameter.

13. The non-pressure continuous blood pressure measuring method according to claim 12, wherein, a frequency band for performing the noise filtering on the reflected pulse wave signal and the electro-cardiac signal is 0.8 Hz to 4 Hz.

14. The non-pressure continuous blood pressure measuring method according to claim 9, wherein, the artery is one or more of aorta and non-aorta.

15. The non-pressure continuous blood pressure measuring method according to claim 9, wherein, the blood pressure parameter comprises a systolic blood pressure, the systolic blood pressure is calculated through a systolic pressure equation, and the systolic pressure equation is:

$$BP_{sys}=a_1\times PWV+b_1$$

wherein, $BP_{sys}$ is the systolic blood pressure; $a_1$ is a pulse wave velocity weighting factor; PWV is a pulse wave velocity; $b_1$ is a linear weighting factor.

16. The non-pressure continuous blood pressure measuring method according to claim 9, wherein, the blood pressure parameter comprises a diastolic blood pressure, the diastolic blood pressure is calculated through a diastolic pressure equation, and the diastolic pressure equation is:

$$BP_{Dia}=a_2\times PWV+b_2$$

wherein, $BP_{Dia}$ is the diastolic blood pressure; $a_2$ is a pulse wave velocity weighting factor; PWV is a pulse wave velocity; $b_2$ is a linear weighting factor.

* * * * *